United States Patent [19]
Brekke

[11] Patent Number: 5,133,755
[45] Date of Patent: Jul. 28, 1992

[54] METHOD AND APPARATUS FOR DIODEGRADABLE, OSTEOGENIC, BONE GRAFT SUBSTITUTE DEVICE

[75] Inventor: John H. Brekke, Duluth, Minn.

[73] Assignee: THM Biomedical, Inc., Duluth, Minn.

[21] Appl. No.: 541,627

[22] Filed: Jun. 21, 1990

Related U.S. Application Data

[63] Continuation of Ser. No. 167,370, Mar. 14, 1988, abandoned, which is a continuation of Ser. No. 823,445, Jan. 28, 1986, abandoned.

[51] Int. Cl.$^5$ .............................................. A61F 2/28
[52] U.S. Cl. ........................................ 623/16; 623/66; 623/11
[58] Field of Search ................... 623/16, 18, 11, 1, 66, 623/22, 23

[56] References Cited

U.S. PATENT DOCUMENTS

| | | |
|---|---|---|
| 3,739,773 | 6/1973 | Schmitt et al. |
| 4,186,448 | 2/1980 | Brekke ................................ 623/16 |
| 4,279,249 | 7/1981 | Vert et al. |
| 4,419,340 | 12/1983 | Yolles |
| 4,442,655 | 4/1984 | Stroetmann ......................... 623/16 |
| 4,609,551 | 9/1986 | Caplan et al. |

*Primary Examiner*—David Isabella
*Attorney, Agent, or Firm*—Peterson, Wicks, Hemer & Kamrath

[57] ABSTRACT

Device and method for treating mammalian bone deficiencies, defects, voids and conformational discontinuities produced by congenital deformities, osseous and/or soft tissue pathology, traumatic injuries and functional atrophy is described. The device is a one piece molded body member composed of four substances, each of which contributes to the device, a specific requirement (or requirements) for osteogenesis and/or osteoneogenesis. Taken as a whole, the functions of these device constituents are integrated into a single body member which, when implanted into a bone defect, has the capacity to restore functional architecture and mechanical integrity, initiate osteoinduction and osteogenesis, and maintain the biological processes of bone formation and remodeling while the host organism is simultaneously biodegrading the body member. The ultimate result of the functioning is formation of healthy, viable bone tissue where there was not bone before, while, simultaneously, the entire device is hydrolyzed and completely metabolized by the host organism. The device comprises four disparate elements: polylactic acid, hyaluronic acid bone morphogenetic protein and bone derived growth factor. Working together, these elements provide the following five biological functions prerequisite to the processes of osteoneogenesis: structural competence (polylactic acid), chemotaxis (hyaluronic acid), electronegative field (hyaluronic acid and physical-chemical electrokinetic events), osteoinduction (bone morphogenetic protein), and osteogenesis (bone derived growth factor).

10 Claims, 2 Drawing Sheets

METHOD AND APPARATUS FOR DIODEGRADABLE, OSTEOGENIC, BONE GRAFT SUBSTITUTE DEVICE

CROSS REFERENCES TO CO-PENDING APPLICATIONS

This application is a continuation of Ser. No. 07/167,370, filed Mar. 14, 1988, expressly abandoned, which is a continuation of application Ser. No. 06/823,445 filed on Jan. 28, 1986, abandoned.

BACKGROUND OF THE INVENTION

1. Field of the Invention

General orthopedic surgery, oral and maxillofacial surgery as a biodegradable medical/surgical device and as a research tool for study of ostenoneogenesis, osteogenesis, cell differentiation, and biochemical cell inductions.

2. Description of the Prior Art

Jarco, M: Calcium phosphate ceramics as hard tissue prosthetics, *Clin. Ortho.*, No. 157, June, 1981, pp. 260-278.

Klawiter, J. J. and Hulbert, S. F.: Application of porous ceramics for the attachment of load bearing internal orthopedic applications, *J. Biomed. Mater. Res. Symposium*, No. 2, (Part I), 1972, pp. 161-229.

Sprinel, L., et al.: Effect of the structure of poly(-glycol mono-methacrylate) gel on the calcification of implants. *Calc. Tiss. Res.*, 13, 1973, pp. 63-72.

Driskell, T. D., et al.: Development of ceramic and ceramic composite devices for maxillofacial applications, *J. Biomed. Mater. Res. Symposium*, No. 2, (Part I), 1972, pp. 91-115.

Brekke, J. H., et. al.: Influence of polylactic acid mesh on the incidence of localized osteitis, *Oral Surg.*, Vol. 56, p. 240-245, Sept. 1983.

Brekke, J. H., et. al.: Effect of surgical trauma and polylactic acid cubes and granules on the incidence of alveolar osteitis in mandibular third molar extraction wounds, *J. Canad. Dent. Assoc.*, In press.

Toole, B. P.: Developmental role of hyaluronate, *Conn. Tis. Res.*, 1982, Vol. 10, pp. 93-100.

Abatangelo, G., et. al.: Healing of hyaluronic acid-enriched wounds: histologic observations, *J. Surg. Research*, 35: 1983, pp. 410-416.

Canalis, E., et. al.: Stimulation of DNA and collagen synthesis by autologous growth factor in cultured fetal rat calvaria. *Science*, Vol. 210 (28): pp. 1021-1023, 1980.

Urist, M. R., et. al.: Human bone morphogentic protein (hBMP), *Proc. Soc. Exp. Bio. Med.*, Vol. 173, pp. 194-199 (1983).

Urist, M. R., et. al.: Beta-tricalcium phosphate delivery system for bone morphogenetic protein. *Clin. Ortho.*, 187, July-Aug., 1984, pp. 277-280.

U.S. Pat. No. 4,186,448, "Device and Method of Treating and Healing a Newly Created Bone Void".

SUMMARY OF THE INVENTION

The gross structure of the body member of the device is composed of a biologically acceptable, biodegradable polymer arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448). Polylactic acid is the polymer currently used to form the gross structure. Other members of the hydroxy acid group of compounds can also be used. The gross, or macro, structure of the invention fulfills three major functions for osteogenesis: 1) restoration of mechanical architectural and structural competence, 2) provides biologically acceptable and mechanically stable surface structure suitable for genesis, growth and development of new non-calcified and calcified tissue, 3) functions as a carrier for other constituents of the invention which do not have mechanical and structural competence.

The microstructure of the body member is composed of a chemotactic ground substance, hyaluronic acid. Interstices of the gross (polylactic acid) structure of the body member are invested with hyaluronic acid in the form of a velour having the same architecture of interconnecting voids as described for the gross structure, but on a microscopic scale. Functions of the hyaluronic acid microstructure are listed as: 1) attraction of fluid blood throughout the device, 2) chemotaxis for mesenchymal cell migration and aggregation, 3) carrier for osteoinductive agent(s), 4) generation and maintenance of an electronegative wound environment, 5) agglutination of other connective tissue substances with each other and with itself. The osteoinductive agent, bone morphogenetic protein, has the capacity to induce primitive mesenchymal cells to differentiate into bone forming cells. Another osteogenic agent, bone derived growth factor, stimulates activity of more mature mesenchymal cells to form new bone tissue.

Significant advantages and features of the present invention include:

1. Eliminate the need to remove autologous bone from the illiac crest or rib for grafting purposes;

2. Functions as part of the internal fixation apparatus to secure itself in the bone void being grafted;

3. Functions as a carrier for biologically active agents (i.e. chemotactic substances);

4. Functions as a carrier for osteoinductive/osteogenic agents, as well as other therapeutic substances (i.e. antibiotics);

5. Creates an electronegative environment which is conducive to osteogenesis in its own right; and, 6. Completely biodegradable; eliminates need for second surgeries to remove device.

Objects of the present invention include:

1. Provide a biodegradable structure to carry and support a chemotactic ground substance which is in the form of a filamentous velour (having incomplete, interconnecting intersticies);

2. Generates electronegative potentials by maintaining an HA-fluid phase and PLA structural phase interface, as well as by the electronegative chemical property of HA alone;

3. Creates biophysical conditions and environment such that exogenous electric signals can be applied to the device (Osmed biodegradable bone graft substitute) to produce a synergistic effect with the endogenous currents generated by HA/PLA surface interactions and the intrinsic electronegativity of HA substance;

4. Granular form—each granule loaded with hyaluronic acid, bone morphogenetic protein and/or bone derived growth factor;

5. Unique juxtaposition of polylactate, hyaluronic acid and chemical osteoinductive/osteogenic agents;

6. Unique arrangement of BGS constituents potentiates osteoinductive effects of exogenous electric potentials and electromagnetic fields; and, 7. Juxtaposition of a chemotactic ground substance with a biodegradable polymer of either solid, open cell meshwork form, or in either form or both forms.

DESCRIPTION OF THE PREFERRED EMBODIMENTS

Figure 1:
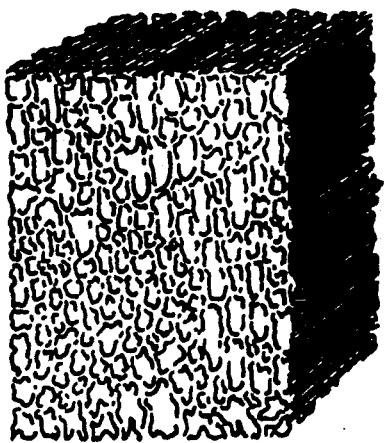
FIG. 1 illustrates a sectional view of the gross structure and architecture of the present invention including randomly shaped, randomly positioned, and randomly sized interconnecting voids.

A device and method are provided for treating mammalian bone deficiencies, defects, voids and conformational discontinuities produced by congenital deformities, osseous and/or soft tissue pathology, traumatic injuries (accidental and/or surgical) and functional atrophy.

The present invention provides a one piece molded body member composed of four substances, each of which contributes to the invention a specific requirement or requirements for osteoneogenesis. Taken as a whole, the functions of these device constituents are integrated into a single body member which, when implanted into a bone defect, has the capacity to restore architectural and structural integrity, initiate osteoinduction, stimulate osteogenesis, and maintain the biological processes of bone formation and remodeling while the host organism is simultaneously biodegrading the body member. The ultimate result of the functioning of this invention is formation of healthy, viable bone tissue where there was not bone before, while, simultaneously, the entire device is hydrolyzed and completely metabolized by the host organism.

The body member is composed of four disparate elements. Each of these entities contributes to the invention essential biologic function or functions prerequisite to the processes of osteneogenesis. There are five such functions listed as follows:

1. Structural Competence—gross structure of the invention restores mechanical, architectural and structural competence to the bone defect while it simultaneously provides mechanical support and structural surface areas for the dynamic biological processes of wound healing and osteogenesis;

2. Chemotaxis—attraction of (mesenchymal) cells of varying degrees of maturation into the wound void from adjacent healthy tissues and from the collateral circulation servicing the wound void;

3. Electronegative Field—production and maintenance of an electronegative environment within the healing bone wound by electrokinetic and electrochemical means;

4. Osteoinduction—production by chemical agents of fundamental genetic changes in primitive mesenchymal cells (perivascular pericytes) such that their future course of maturation is predetermined to result in their transformation into mature bone forming cells (osteoblasts).

5. Osteogenesis—stimulation of biosynthetic processes of cells already induced to mature as osteoblasts.

Each of the body member constituents and their osteogenic functions are described in the following sections; first in general terms, then in specific detail.

Elements and Biological Functions of Body Member Constituents

Biodegradable Polymeric Macrostructure

The gross structure of the body member is composed of a biologically acceptable, biodegradable polymer arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448).

The material currently used to form the gross structure is the polymer of lactic acid (polylactic acid). This is a specific example of a biodegradable polymer. Lactic acid is a member of the hydroxy acid group of organic compounds. Other members of this group, such as glycolic acid, malic acid and alpha hydroxybutyric acid, can also be polymerized into biodegradable polymer suitable for use in the gross structure of this invention. In addition, compounds of other metabolic pathways, such as fumaric acid, can be polymerized and used in similar manner.

The gross structure is composed of a poly(hydroxy) acid and in the form of an interconnecting, open-cell meshwork, duplicates the architecture of human cancellous bone from the illiac crest and possesses physical property (strength) values in excess of those demonstrated by human (mammalian) illiac crest cancellous bone. The gross structure of the invention maintains physical property values at least equal to those of human, illiac crest, cancellous bone for a minimum of 90 days following implantation.

Biodegradable Macrostructure

The gross, or macro, structure of the invention fulfills three major functions required for osteogenesis. These functions are:

1. restoration of mechanical, architectural and structural competence to the bone void being treated;
2. providing a biologically acceptable and mechanically stable surface structure suitable for genesis, growth and development of new non-calcified and calcified connective tissue;
3. acting as a carrier for the other constituents of the invention which do not have mechanical and structural competence.

Biodegradation of the hydroxy acids is initiated by the process of hydrolysis. The polymer, at body temperature, takes on water and is first hydrolyzed to the dimer of lactic acid, lactide. Lactide units are further hydrolyzed to free lactic acid which is then incorporated into adjacent cells and metabolized, via the Kreb's Cycle, to energy (in the form of adenosine triphosphate), water and carbon dioxide.

Biodegradable Polymeric Microstructure

The microstructure of the body member is composed of a chemotactic ground substance. Glycoproteins such as collagen and fibronectin would be suitable chemotactic ground substances for this invention. The glycosaminoglycan, hyaluronic acid, is another suitable chemotactic ground substance for this device. Hyaluronic acid is the chemotactic ground substance of choice because it is commercially available in quantity and because it possesses several favorable properties in addition to its chemotactic qualities.

Hyaluronic acid is a prime constituent of all naturally occurring, mammalian connective tissues (calcified as well as non-calcified connective tissues). The hyaluronic acid used can be synthesized by bacteria such as that used in known processes. Following purification of the material, the hyaluronic acid can be processed into a velour composed of hyaluronate fibrils with intercalated voids of microscopic dimensions. Each void communicates with all others within the hyaluronate velour.

Interstices of the gross (polylactic acid) structure of the body member are invested with chemotactic ground substance, such as the velour of hyaluronic acid. In final form, the velour of chemotactic ground substance completely occludes all of the interstices of the polylactic acid macrostructure of the body member.

The velour of chemotactic ground substance (hyaluronic acid) accomplishes several biochemical and biomechanical functions essential for bone wound healing and osteogenesis. These functions, five in number, are listed as follows:

1. Attraction of Fluid Blood—Hyaluronic acid is extremely hydrophilic. It is capable of taking on between 500× and 1,000× its own weight in water. It does, therefore, attract any water based fluid, such as whole blood, blood plasma and serum. This quality of hyaluronate is valuable for drawing fluid blood to all regions of the bone void being treated and establishing a viable blood clot in all areas of the bone void in question.

2. Chemotactic for Mesenchymal Cell Migration and Aggregation—By virtue of its hydrophilia and by virtue of specific cell binding cites, hyaluronic acid is an important matrix (or substrate) for embryonic and wound healing mesenchymal cell migrations, proliferations and aggregations. Its presence facilitates movement of undifferentiated mesenchymal cells from their points of origin in surrounding healthy tissues and collateral circulation to all regions of the bone void under treatment.

3. Carrier for Osteoinductive/Osteogenic Agent(s)—By chemical binding, as well as by mechanical entrapment, hyaluronic acid is capable of being joined to osteoinductive/osteogenic agents such as the bone morphogenetic protein (BMP) and the bone-derived growth factor (BDGF).

4. Generation and Maintenance of an Electronegative Environment—The chemical, hyaluronic acid, is strongly electronegative. Its presence in a fresh wound will, by chemical means, cause the wound environment to be electronegative. When saturated with fluid blood (80% water), the hyaluronate velour becomes a highly viscous gel or plasma with an electronegative charge. An electrokinetic event is generated at the interface of the hyaluronate plasma and the polylactate of the macrostructure whenever there is a slight structural distortion of the body member. The electrokinetic event is a second source of electronegativity related to, but independent from, the electronegative chemical properties of hyaluronic acid.

5. Agglutinate Other Connective Tissue Substances with Each Other and with Itself—Hyaluronic acid is the core protein of glycosaminoglycan and proteoglycan aggregates. It also binds, by virtue of specific receptor sites, to the glycoproteins (specifically collagen, fibronectin and osteonectin) and to the pericellular matricies of undifferentiated mesenchymal cells and mature connective tissue cells.

This wide variety of connections to cells, as well as to the prime constituents of the intercellular matrix, makes hyaluronic acid one of the central players (participants) in the growth, development and maintenance of mature connective tissue of both non-calcified and calcified varieties.

Hyaluronic acid is hydrolyzed by the enzyme, hyaluronidase. This enzyme is produced in the lysosomes of the cells which develop within the hyaluronate polymer matrix.

Osteoinductive/Osteogenic Substance(s)

Located within the organic phase of bone tissue are substances which have the capacity to induce primitive mesenchymal cells to differentiate into bone forming cells (osteoblasts) or stimulate activity of more mature mesenchymal cells. These substances are present in all normal, viable bone tissues as well as in autologous, allogeneic and xenogeneic bone graft specimen.

At least two such substances have been identified, isolated, purified, and partially characterized. One of these is the bone-derived growth factor (BDGF); the other is the bone morphogenetic protein (BMP). Predifferentiated cartilage or osteoprogenetor cells are the target cells for BDGF. BDGF is a paracrine-autocrine substance that increases activity of already active desoxyribonucleic acid (DNA) sequences to accelerated activities and rates of replication, presumably by releasing controls or constraints that would normally hold these genes in check. Bone morphogenetic protein (BMP) has, as its target cell, mesenchymal cells which are very primitive, having little or no degree of differentiation. These are known as perivascular parasites. BMP initiates activity of entirely new DNA sequences within these cells which lead to genesis of an entire embryonic type bone synthesis program.

Either or both of these substances is incorporated into the hyaluronic acid microstructure immediately prior to implantation of the device into bone void being treated. By this means these agents are evenly distributed throughout the volume of the body member and are, therefore, evenly distributed throughout the bone void being treated.

Where ever a perivascular pericyte, migrating on the hyaluronic acid microstructure, comes in contact with bone morphogenetic protein (bound to the hyaluronic acid microstructure) a new locus of osteogenesis will be formed. Likewise, osteogenesis will be accelerated where ever a more differentiated cartilage or osteoprogenetor cell contacts bone-derived growth factor in the hyaluronic acid microstructure.

FIG. 1 is a sectional view of the gross structure and architecture of the present invention consisting of randomly shaped, randomly positioned, randomly sized interconnecting voids. The incomplete partitions of these voids are composed of biodegradable structural polymer. In the case of this device, that structural polymer is polylactic acid. In this figure, as well as in FIG. 2, the randomly sized, shaped and positioned voids are empty.

Figure 2:
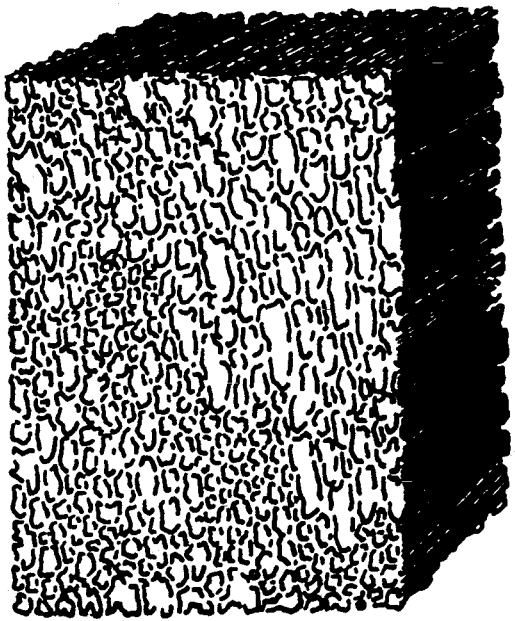
FIG. 2 is an enlarged view of FIG. 1.

FIG. 2 is an enlarged view of FIG. 1 to demonstrate more clearly the interconnecting void architecture of the structural polymer.

Figure 3:
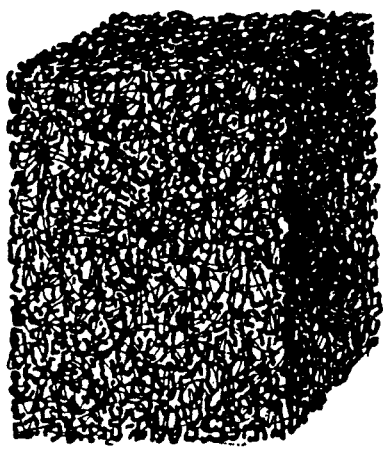
FIG. 3 is a sectional view of the gross polymeric structure after the voids of the gross structure have been invested with velour of chemotactic ground substance.

FIG. 3 is a sectional view of the gross polymeric structure shown in FIG. 1 after the voids of the gross structure have been invested with a velour of chemotactic ground substance, such as a glycosaminoglycan or glycoprotein—specifically hyaluronic acid or fibronectin. The dark heavy lines represent the structural biodegradable polymer, polylactic acid, while the fine line network represents the velour of chemotactic ground substance, i.e. hyaluronic acid.

Figure 4:
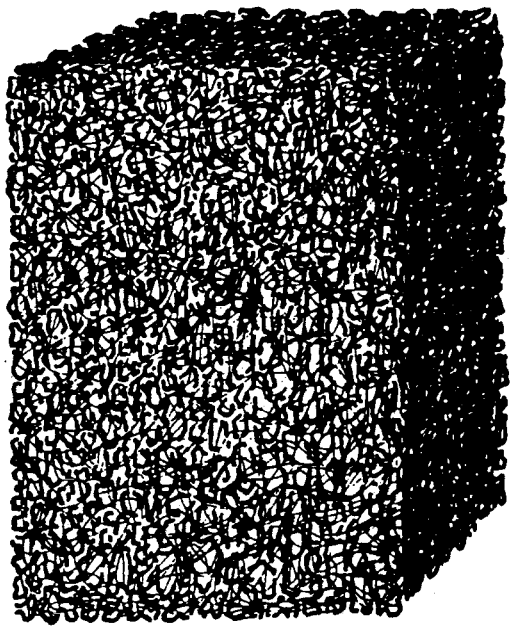
FIG. 4 is an enlarged view of FIG. 3.

FIG. 4 is an enlarged view of FIG. 3 to demonstrate more clearly the relationship between the gross polymeric structure of the device composed of polylactic acid and the micro-structure of the device composed of a filamentous network of chemotactic ground substance. The velour of chemotactic ground substance coats all surfaces of the gross structural polymer with a dense network of glycosaminoglycan or glycoprotein fibrils. This same velour of chemotactic ground substance fills or occludes all void areas between structural polymer partitions with a network of glycosaminoglycan or glycoprotein fibrils. The fibrillar network of chemotactic ground substance velour coating the surfaces of structural polymer is identical with and continuous with the fibrillar network of chemotactic ground substance velour which occludes the voids partioned by the structural polymer.

Figure 5:
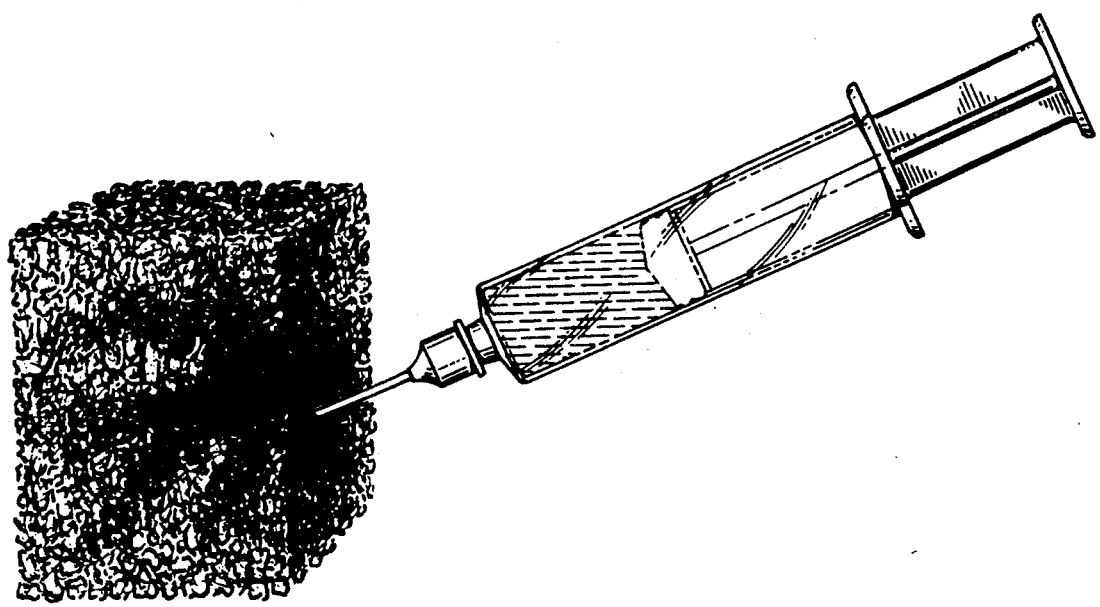
FIG. 5 is a sectional view of the FIGS. 3 and 4.

FIG. 5 is a sectional view of the device as shown in FIGS. 3 and 4. In this instance the device is being infused with a solution of biologically active agent or agents i.e. the osteoinductive agent known as bone morphogenetic protein. This solution is dispersed throughout the volume of the device, enveloping all of the fibrils of the chemotactic ground substance velour and coating all surfaces of the structural polymer.

Figure 6:
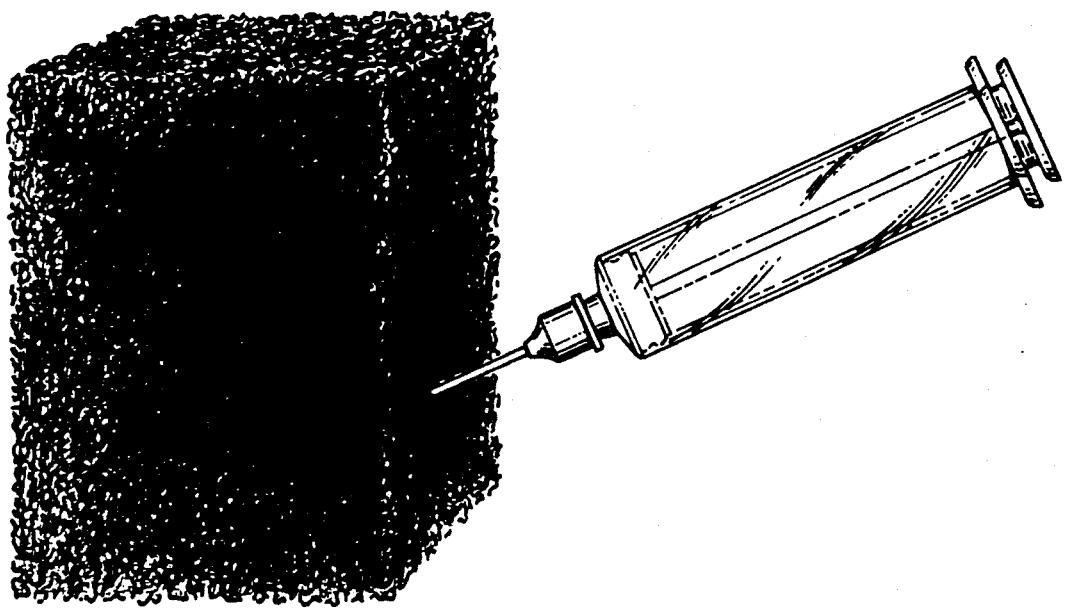
FIG. 6 is an enlarged view of FIG. 5.

FIG. 6 is an enlarged view of FIG. 5 to demonstrate more clearly the infusion of biologically active agent solution into the device and the dispersion of this solution throughout the entire volume of the body member.

The device facilitates the healing of structural voids in bone and includes a gross structure made from a biodegradable element, providing architecture and structural/mechanical integrity to the bone void being treated; a micro-structure formed from a chemotactic ground substance and integrated throughout spaces in the gross structural component; and a biologically active agent (or agents) and/or therapeutic agent (or agents) carried by either the gross or micro-structural elements or at the interface between the gross and micro-structural components.

The device also facilitates the healing of structural voids in bone and includes a gross structure formed from a biodegradabe polymer which is either a homogeneous poly(hydroxy) acid or a co-polymer of two or more poly(hydroxy) acids; a micro-structure formed from a chemotactic ground substance, specifically, a glycosaminoglycan(s) and/or a glycoprotein(s) or a combination of these substances; and biologically and/or therapeutically active agent(s), specifically, an osteoinductive substance known as the bone morphogenetic protein and an osteogenic substance known as the bone-derived growth factor.

The device facilitates the healing of structural bone defects whose gross structure, composed of a biodegradable polymer such as polylactic acid, is in the form of partially "enclosed, interconnected, randomly positioned and randomly sized and shaped voids; each void connecting with the others and communicating with the exterior of the body" (quoted portion from U.S. Pat. No. 4,186,448). The device also facilitates the healing of structural bone defects whose micro-structure, composed of a biodegradable chemotactic ground substance such as the glycosaminoglyca known as hyaluronic acid or the glycoprotein known as fibronectin, is likewise in the form of partially complete, interconnecting, randomly positioned and randomly sized and shaped intersticies; each interstice connecting with all the others and communicating with any exterior location of the chemotactic ground substance.

The device also facilitates the healing of structural bone defects in which the filamentous velour of chemotactic ground substance is invested into the interconnecting voids (intersticies) of the polymeric gross structure.

Juxtaposition of different forms of the constituent elements occurs as solid form of structural polymer with open-cell meshwork (velour) form of the chemotactic ground substance; solid form of chemotactic ground substance with open-cell meshwork (velour) form of structural polymer; and solid form of chemotactic ground substance with solid form of structural polymer.

Therapeutic and/or biologically active agent(s) can be carried by the structural polymer. Therapeutic and/or biologically active agent(s) can be carried by the chemotactic ground substance. Therapeutic and/or biologically active agent(s) can be carried by entrapment between the chemotactic ground substance and the structural polymer at their interface.

MODE OF OPERATION

The net result of these biological activities is establishment of multiple foci of osteogenesis within the implanted body member. As these individual foci of osteogenesis enlarge they coalesce into larger volumes of new bone tissue. Simultaneously, cells involved in the osteogenic process are metabolizing free lactic acid that is constantly generated by hydrolysis of the polylactic acid macrostructure. These same cells are also producing the enzyme, hyaluronidase, which hydrolyzes hyaluronic acid. The osteoinductive/osteogenic agents are metabolized by the cells to which they become attached.

Ultimately the polylactate macrostructure and the hyaluronate microstructure are hydrolyzed and metabolized by the variety of mesenchymal cells which compose the genealogy of the osteoblasts, by various scavenger cells such as macrophages and by occasional foreign body giant cells. The bone void volume formerly occupied by constituents of the body member becomes progressively occupied by new bone generated from the multiple foci of osteoneogenesis initiated in the hyaluronic acid microstructure by osteoinductive/osteogenic agents.

The device is applied in the same manner as any autologous or allogeneic bone graft material. Just before insertion into the bone void being grafted, the macro and micro-structure complex is injected with a solution of sterile water, plasma or serum containing the osteoinductive and/or osteogenic agent (bone morphogenetic protein and/or bone derived growth factor) rather than simply moistening it with sterile saline, whole blood or blood plasma as is current practice.

Various flanges, rods, bars and other appendages are used to affix the macrostructure of the device to surrounding healthy bone using wires, screws (also of polylactic acid) and PLA staples and sutures.

The macro-structure is formed by a vacuum foaming process using an adaptation of standard lyophilization techniques.

The micro-structure is formed by lyophilization of the alcohol gel solution of hyaluronic acid after the interstices of the macrostructure have been invested with the HA gel.

The osteoinductive/osteogenic agent is injected into the PLA/HA complex structure immediately before the device is inserted into the bone void being treated. This is done by the operating surgeon or a surgical assistant.

The open-cell meshwork architecture of hyaluronic acid polymer is composed of hyaluronate in the form of a filamentous velour. This velour is characterized by randomly positioned, randomly shaped and randomly sized voids all of which are incompletely partitioned. These incomplete voids are, in fact, intercommunicating interstices each of which communicates with all of its neighboring voids and possesses and unimpeded avenue of communication with any point on the surface of the hyaluronic acid portion of the device.

Utilizing the hydrophilic properties of hyaluronic acid, a sterile solution of biologically active agent (in this case the bone morphogenetic protein and/or bone derived growth factor) is evenly distributed throughout the volume of the device and the agent itself is attached to the hyaluronic acid velour such that cells invading the device are attracted to the substance and held in contact with it by virtue of hyaluronate's chemotactic properties.

Hyaluronic acid is strongly electronegative. Electronegative wound environments have been demonstrated to be favorable for osteogenesis. By virtue of its electronegative properties and its uniform, wide spread distribution throughout the volume of the device (and, therefore, the volume of the wound), hyaluronate, in the form of an open-cell velour, creates an electronegative wound field until it is biodegraded past a critical minimum concentration.

Examples of chemotactic ground substances are: hyaluronic acid and fibronectin. Examples of biodegradable structural polymers are: the poly(hydroxy) acids (i.e. polylactic acid, polyglycolic acid) and polysulfone.

Various modifications can be made to the present invention without departing from the scope thereof.

What I claim is:

1. A composition comprising a functional juxtaposition of a biodegradable polymer and a chemotactic ground substance fabricated together in such a manner as to produce a biodegradable and biologically inductive surgical implant which performs to restore a tissue void to its normal gross morphology, structural architecture, mechanical competence, biologic and physiologic activities, cell populations and biochemical functions, with the biodegradable polymer arranged as a gross structure with interconnecting voids, generally with each void communicating with all the others and with substantially the entire exterior of the gross structure, with the chemotactic ground substance located in the voids and carried by and seperate from the biodegradable polymer forming the gross structure.

2. The composition of claim 1 in which the chemotactic ground substance is selected from the group of:
    a. a solid sheet adhered to the preformed partitions of the biodegradable polymer;
    b. an open laced network of strands adhered to the preformed biodegradable polymer partitions;
    c. a velour, felting or loosely woven sheet adhered to the preformed biodegradable polymer partitions; or,
    d. an open cell meshwork mass that is carried within the voids of the gross structure and is only incidentally adhered to the preformed biodegradable polymer partitions.

3. The composition of claim 1 further comprising at least one biological modifier incorporated into the implant selected from the group of:
    a. joined to the surface of the biodegradable polymer partitions;
    b. joined to the chemotactic ground substance;
    c. located between the biodegradable polymer and the chemotactic ground substance at the interface of these components; or,
    d. carried within the chemotactic ground substance.

4. The composition of claim 1 in which the biodegradable polymer is synthesized either as a homogeneous polymer or as a co-polymer of at least two alphahydroxy acids.

5. The composition of claim 4 wherein said biodegradable polymer is selected from the group of D,L-polylactic acid, L-polylactic acid, glycolic acid or co-polymers thereof.

6. The composition of claim 1 in which the chemotactic ground substance microstructure is selected from the group of glycosamino glycans, glycoproteins, lamin or type IV collagen.

7. The composition of claim 3 in which the biological modifier is osteoinductive/osteogenic agents selected from the group of bone morphogenetic proteins or bone derived growth factor.

8. The composition of claim 1 wherein the biodegradable polymer is preformed into the gross structure prior to the introduction of the chemotactic ground substance.

9. The composition of claim 8 wherein the chemotactic ground substance is selected from the group of a velour, felting or loosely woven sheet prior to its introduction into the gross structure, with the velour, felting, or loosely woven sheet adhered to the preformed gross structure of the biodegradable polymer within the voids of the gross structure.

10. The composition of claim 8 wherein the voids are randomly shaped, sized and positioned in the gross structure, with the voids being formed by incomplete partitions of the biodegradable polymer.

* * * * *

UNITED STATES PATENT AND TRADEMARK OFFICE
CERTIFICATE OF CORRECTION

PATENT NO. : 5,133,755
DATED : July 28, 1992
INVENTOR(S) : John H. Brekke It is certified that error appears in the above-identified patent and that said Letters Patent is hereby corrected as shown below:

Cover Page, Title Line, cancel "DIODEGRADABLE" and substitute therefor --BIODEGRADABLE--.

Cover Page, Attorney, Agent, or Firm Line, cancel "Hemer" and substitute therefor --Nemer--.

Column 1, line 2, cancel "DIODEGRADABLE" and substitute therefor --BIODEGRADABLE--.

Column 6, line 5, cancel "-".

Column 10, line 4, cancel "1" and substitute therefor --10--.

Column 10, line 17, cancel "1" and substitute therefor --10--.

Signed and Sealed this

Twentieth Day of September, 1994

Attest:

BRUCE LEHMAN

Attesting Officer

Commissioner of Patents and Trademarks